United States Patent [19]

Barclay

[11] 3,976,057
[45] Aug. 24, 1976

[54] JOINT FLEXING APPARATUS

[75] Inventor: Doltie W. Barclay, Ilion, N.Y.

[73] Assignees: Clarence F. Bates, Middleville; William D. Heron, Little Falls; Gerald E. Bates, Utica; Irving Mason, Herkimer, all of N.Y. ; part interest to each

[22] Filed: Dec. 23, 1974

[21] Appl. No.: 535,704

[52] U.S. Cl. ............................. 128/25 R; 272/130
[51] Int. Cl.² ............................................ A61H 1/02
[58] Field of Search ........ 272/79 C, DIG. 1, DIG. 4, 272/72, 80, 58, 67, 68, 70, 76; 128/25 R, 25 B; 16/49; 184/18; 251/15

[56] References Cited
UNITED STATES PATENTS

| | | | |
|---|---|---|---|
| 767,008 | 8/1904 | Pelletier et al. | 272/79 C |
| 2,058,563 | 10/1936 | Campbell | 128/25 |
| 2,068,578 | 1/1937 | Stronach | 272/79 |
| 2,179,903 | 11/1939 | Spears | 128/80 |
| 2,180,173 | 11/1939 | Share | 251/15 X |
| 2,825,563 | 3/1958 | Lawton | 272/79 |
| 2,966,905 | 1/1961 | Kamenshine | 128/25 |
| 3,000,632 | 9/1961 | Fuchs | 272/58 |
| 3,117,786 | 1/1964 | Anderson | 273/54 |
| 3,174,343 | 3/1965 | Kasulis | 73/379 |
| 3,346,877 | 10/1967 | Zirves | 2/24 |
| 3,351,156 | 11/1967 | Cook et al. | 184/18 X |
| 3,369,403 | 2/1968 | Carlin et al. | 73/379 |
| 3,387,843 | 6/1968 | Chandler | 272/79 |
| 3,406,406 | 10/1968 | Lutz | 2/24 |
| 3,471,145 | 10/1969 | Berger | 272/79 |
| 3,531,112 | 9/1970 | Gibbs | 272/79 |
| 3,659,846 | 5/1972 | Kanicki | 272/80 |
| 3,683,897 | 8/1972 | Shield et al. | 128/25 R |
| 3,814,419 | 6/1974 | Bjorklund et al. | 272/80 |
| 3,837,432 | 9/1974 | McKendrick | 184/18 X |

*Primary Examiner*—Richard C. Pinkham
*Assistant Examiner*—William R. Browne
*Attorney, Agent, or Firm*—Roylance, Abrams, Berdo & Kaul

[57] ABSTRACT

A flexing apparatus including first and second straps to encircle the body above and below a joint, pivotable links between the straps to maintain alignment between them and piston and cylinder assemblies extending between the straps. Adjustable bleed valves in the cylinder ends provide calibrated leakage to present resistance to flexion and extension of the joint. An air supply and control are attached to the cylinder ends to provide controlled power flexion and extension of the joint for therapy, including a compressor, air filtering, regulating and lubricating devices, a two position solenoid operated valve and an electrical timing and switching circuit for energizing the solenoid.

5 Claims, 6 Drawing Figures

JOINT FLEXING APPARATUS

This invention relates to therapeutic apparatus for exercising a body joint by flexion and extension thereof.

In the case of certain forms of physical trauma or following surgery or other medical techniques or illnesses related to muscle, tendon and bone structure of a joint, it is necessary to flex the joint under controlled conditions as prescribed by the attending physician. Depending upon the specific medical condition, this exercise may take several forms. Following certain kinds of surgery, for example, on a knee joint, the patient is instructed to flex the joint with weights placed upon the foot with the patient sitting upon a table or other surface which is sufficiently high to prevent the foot from coming in contact with the floor. The foot is elevated and varying amounts of weight can be placed on the foot to provide the desired resistance to motion, thereby building up injured muscle and other tissue until the knee reaches a fully usable condition.

In other situations it is necessary to employ external force to flex and extend the body portion surrounding the joint, sometimes while the patient is immersed in a hydrotherapeutic bath. Under these circumstances, it is common practice to immerse the patient in a bath of swirling water, sometimes at elevated temperature, while a physical therapist carefully moves the limbs, flexing and extending the joint to induce motion and prevent development of a locked condition in the joint. Therapy following illnesses such as poliomyelitis and multiple sclerosis also involves application of external force to a limb to cause it to move, thereby flexing and exercising the affected joint or joints to promote repair thereof.

These procedures frequently involve care by a physical therapist and occupy substantial time, effort and attention with each patient.

In addition, exercise involving the use of weights on the foot is frequently quite difficult and clumsy because of the necessity of maintaining the body portions surrounding the joint in a specific orientation so as to make good use of gravitational forces, these positions not necessarily being the most desirable positions in which to maintain the joint for comfort of the patient as well as for maximum therapeutic effect.

An object of the present invention is to provide an exercising device capable of exerting calibrated and adjustable resistance to movement of a joint such as a knee or elbow while performing the desired exercises.

A further object is to provide an apparatus capable of applying external force to the body portions on either side of the affected joint to accomplish predictable and adjustable flexion and extension thereof in a gentle and effective manner while relieving the attending physical therapist from some of the labors attendant thereto so that the time and knowledge of such experienced and skilled personnel can be better employed with multiple patients.

Broadly described, the apparatus constitutes a device for exercising a body joint such as a knee or elbow and comprises a first strap means for encircling the body near and on one side of a joint to be exercised, second strap means for encircling the body near and on the other side of the joint to be exercised, and fluid resistance means connected between the first and second strap means for resisting flexion and extension of the body joint. Linkage means can be provided between the two strap means to maintain them in predetermined relationship with each other and with the joint, the linkage means having link portions joined at a pivot point, coinciding generally with the pivot axis of the joint, for permitting relative pivotal motion of the link portions corresponding to motion of the body portions joined at the joint to be exercised. The fluid resistance means is advantageously a pneumatic piston and cylinder assembly having adjustable valve means at each end thereof for controlling the air flow into and out of the cylinder. Basically the same apparatus can be employed in conjunction with a source of fluid under pressure and valve and control means for controlling the application of fluid from the source to the same apparatus which was used as the fluid resistance means, this apparatus becoming, in this application, a fluid drive means connected between the strap means for moving the straps and, thereby, the body portion to flex and extend the joint. The valve and control means can further include means for adjusting the pressure of fluid, such as air, directed to the cylinder, having solenoids and a positionable valve to control the sequence and interval of pressure application, along with timing means to establish these intervals.

In order that the manner in which the foregoing and other objects are attained in accordance with the invention can be understood in detail, particularly advantageous embodiments thereof will be described with reference to the accompanying drawings, which form a part of this specification, and wherein.

Figure 1:
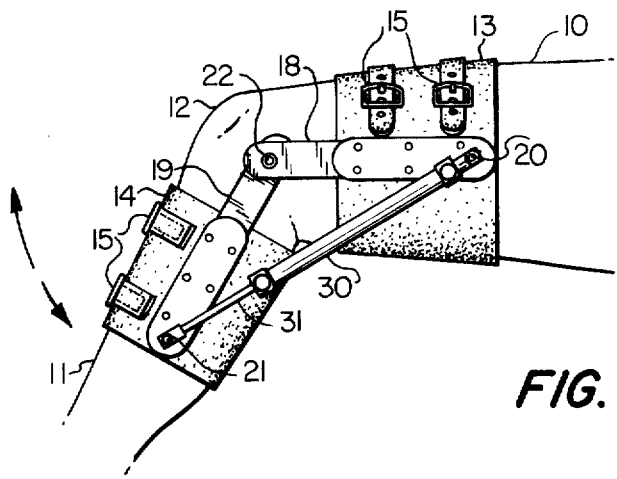
FIG. 1 is a side elevation of an exercising apparatus according to the invention, shown in the environment of a knee joint to be exercised.
Figure 2:
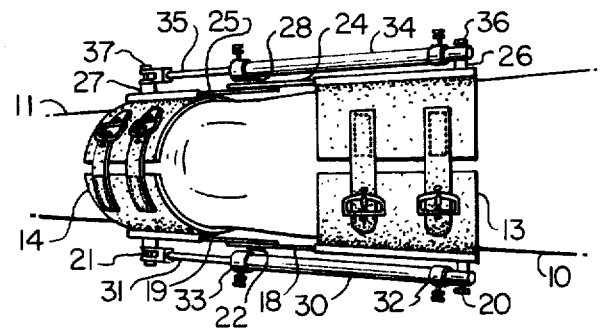
FIG. 2 is a plan view of the apparatus and environment of FIG. 1.

Referring first to FIGS. 1 and 2, it will be seen that the apparatus is shown in the environment of a portion of the body comprising a thigh 10 and lower leg 11 joined at the knee 12, the joint to be exercised constituting the movable articulation of the femur and tibia with the associated tendons, ligament and cartilage. For purposes of exercising the joint, the apparatus of the invention includes upper strap means 13 and lower strap mean 14, these strap means encircling the thigh and lower leg, respectively. The strap means 13 includes a strap fabricated from a heavy fabric such as canvas or the like and provided with buckles 15 or other fastening means. The strap is sufficiently flexible so that it can be placed around the thigh, adjusted to the dimensions of the limb of the specific patient, and secured in a position so that it will remain where placed without discomfort. Stiffening pads or ribs of leather and plastic or comfort pads on the interior of the strap to come in contact with the limb can also be provided, but these will not be described in further detail as they do not constitute a part of the present invention.

In order to maintain the strap means in the proper relative location with respect to each other and with respect to the joint in the vicinity of which they are placed, there are linkage means provided, preferably on both sides of the joint to avoid any difficulty arising from uneven distribution of forces. The linkage means includes an upper link 18 and a lower link 19, each of these links being secured to its associated one of the strap means at points 20 and 21, respectively. It should be noted that the links are connected to the straps in a position so that they extend approximately parallel to the major bone within each limb. Thus, link 18 is attached to strap 13 so as to be substantially parallel with the femur while link 19 is attached to strap 14 in a position essentially parallel with the tibia and, therefore, with the fibula. These links are attached so as to maintain these relative positions and are not pivotally connected to their associated straps. They are, however, connected to each other at a pivot point 22 and are therefore freely pivotable with respect to each other. In the initial placement of the apparatus on the body, the straps and links are adjusted so that pivot point 22 is as closely as possible aligned with the axis of the knee joint about which the bones joined thereat rotate.

As seen in FIG. 2, a similar linkage arrangement is provided on the opposite side of the limb, including an upper link 24 and a lower link 25 joined to the opposite sides of straps 13 and 14 at points 26 and 27, respectively. Links 24 and 25 are pivotally joined at a pivot point 28.

Connected between points 20 and 21 there is provided a piston and cylinder assembly including a cylinder 30 having one end pivotally connected to point 20, the cylinder having a piston therein with a connecting rod 31 extending through the other end of cylinder 30 and pivotally attached at point 21. The piston and cylinder arrangement constitutes the variable length base of an isosceles triangle, the equal legs of which are formed by links 18 and 19. Adjustable valves and air inlet means, to be described in greater detail hereinafter, are provided at ends 32 and 33 of cylinder 30.

A substantially identical apparatus can be provided on the opposite side of the joint including a cylinder 34 containing a piston having a connecting rod 35, cylinder 34 being pivotally connected at point 36 on strap 13 at the end of link 24, the connecting rod 35 being pivotally connected at point 37 at strap 14 and the end of link 25. This piston and cylinder assembly similarly forms the variable length base of an isosceles triangle mathematically similar to that previously described in which the equal length legs are formed by links 24 and 25.

It will be understood that an apparatus of this general type can be constructed using only one piston and cylinder arrangement on one side of the joint. However, for equalization of the forces, and to prevent any lateral torque on the joint being exercised, it is considered preferable to provide two identical arrangements.

Figure 3:
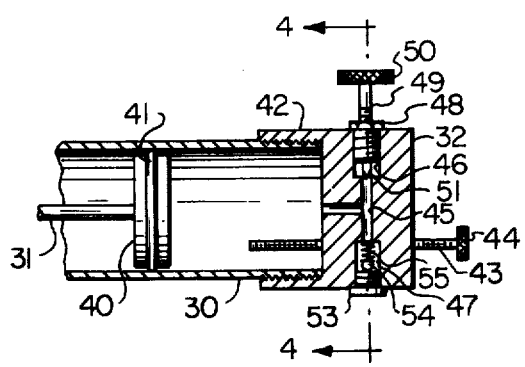
FIG. 3 is a detail, inside elevation, of one portion of the piston and cylinder apparatus usable in the device of FIGS. 1 and 2.

One end of the piston and cylinder arrangement is shown in FIG. 3. End 32 of cylinder 30 is illustrated, but a substantially identical structure exists at end 33 of cylinder 30 and at the ends of cylinder 34, the sole difference being that at end 33 of cylinder 30 and at the corresponding end of cylinder 34 there is provided an opening through which connecting rods 31 and 35 pass, these openings being provided with sliding seal arrangements of a conventional nature to prevent undesirable escape of air pressure therefrom.

As shown in FIG. 3, connecting rod 31 is connected to a piston 40 which is surrounded by an annular O-ring seal 41 so that the piston is in airtight sliding relationship with the interior surface of cylinder 30.

The end of cylinder 30 can be externally threaded to receive an internally threaded skirt 42 integrally formed with end 32. A mechanical stop member 43 extends through end 32. Member 43 is externally threaded in the nature of an elongated machine screw and passes through a threaded opening in end member 32 so as to be adjustable therein, the internal end thereof constituting an abutment stop limiting the degree of motion of piston 40 within the cylinder. Stop member 43 has an enlarged end 44 which can be manually rotated to adjust the stop member.

End member 32 is provided with internal conduits 45 which communicate with the interior of cylinder 30 and with chambers 46 and 47 which contain air flow controlling valve means. Chamber 46 is internally threaded to receive an externally threaded valve sleeve 48 which includes air channels to permit air flow between chamber 46 and the ambient atmosphere. The interior of the sleeve is also threaded to receive a needle valve 49 having an enlarged knob end 50. The inner distal end 51 of the needle valve is pointed and protrudes into conduits 45 at the junction of the conduits with chamber 46. End 51 and the end of the chamber thus form a valve and seat arrangement through which the passage of air flow is controlled by adjustment of valve 49 by manual rotation of knob 50.

Chamber 47 includes an externally threaded sleeve 53 which has a central open bore. At the inner end of the bore in sleeve 53 is a ball 54 which is held against the inner end of the bore by a compression spring 55, thus preventing air flow out of the conduit and chamber and permitting air flow into the chamber only when the difference between atmospheric pressure and the pressure within the chamber is sufficient to permit compression of the spring and separation of the ball from the inner end of the bore. As will be recognized, this is a conventional form of check valve.

Figure 4:
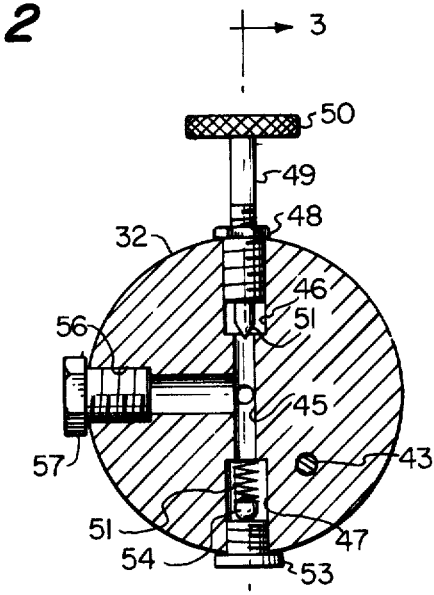
FIG. 4 is an end view, in section, of the apparatus of FIG. 3.

As also seen in FIG. 4, conduits 45 also lead to a chamber 56 which is internally threaded to receive a plug 57. Plug 57 can be a solid plug capable of preventing air flow therethrough or it can be a coupling plug to which a conduit can be quickly connected. If it is a solid plug, a connection is made by removing the plug and replacing it with an externally threaded conduit connector of conventional type. In either event, the plug is formed so that air flow therethrough is not possible in either direction unless a conduit is connected thereto or replaces the plug. This plug and its associated chamber are not necessary in the device used as shown in FIG. 1 to provide fluid resistance, but is usable in connection with the driven apparatus to be described hereinafter.

Figure 5:
FIG. 5 is a schematic diagram showing the pneumatic operation of the apparatus of FIGS. 3 and 4 as employed in FIGS. 1 and 2.

A schematic representation of the piston and cylinder arrangement is shown in FIG. 5 wherein there is illustrated a cylinder 60, a piston 61, a connecting rod 62 and pivotal connection means 63 and 64, connectable to the pivot points on the straps as previously described. Mechanical stops 65 and 66 extend through the ends of the cylinder. At the ends of the cylinder are check valves 67 and 68 of a type which permit air flow into the cylinder only. Also at the ends of the cylinder are adjustable bleed valves 69 and 70 equivalent to the needle valves 49 described with reference to FIGS. 3 and 4. The functional schematic representation of FIG. 5 is provided to enhance the understanding of the operation in which the apparatus is employed to provide fluid resistance to joint flexion and extension. Assuming that pivot point 63 is connected to a strap below the knee and pivot point 64 is connected to a strap above the knee, flexion of the joint tends to move points 63 and 64 toward each other, moving piston 61 toward mechanical stop 66. The motion in this direction is controlled by the flow of air through bleed valve 70 which is adjusted to provide the desired amount of resistance, i.e., sufficient resistance to necessitate exercise of the joint but not such a high level of resistance as to cause potential damage. Check valve 67 permits air flow into the cylinder to prevent the development of a vacuum behind the cylinder which would affect the control function of bleed valve 70.

For movement in the opposite direction, i.e., extension of the limb, piston 61 tends to move toward stop 65 and the motion in this direction is resisted by pressure created in that end of the cylinder, the air flow therefrom being controlled by the adjustment of bleed valve 69. Check valve 68 permits entry of air into the opposite end of the cylinder in the same manner as valve 67. Motion in either direction continues until the natural flexion or extension limit of the joint is reached or until the mechanical stop is contacted by the piston, which ever occurs first. It will be noted that during flexion air flow into the cylinder also occurs through valve 69 and it may be that the check valve would never operate. The analogous situation exists in extension. However, the provision of the check valves permits different adjustments of the bleed valves so that greater resistance might be provided against flexion than against extension, the check valve in one or the other case preventing either valve from controlling at a lower flow setting.

As previously indicated, it is contemplated that two piston and cylinder assemblies such as shown in FIGS. 1–4 and described with reference to FIG. 5 would be provided, the adjustment thereof and function thereof being identical.

Figure 6:
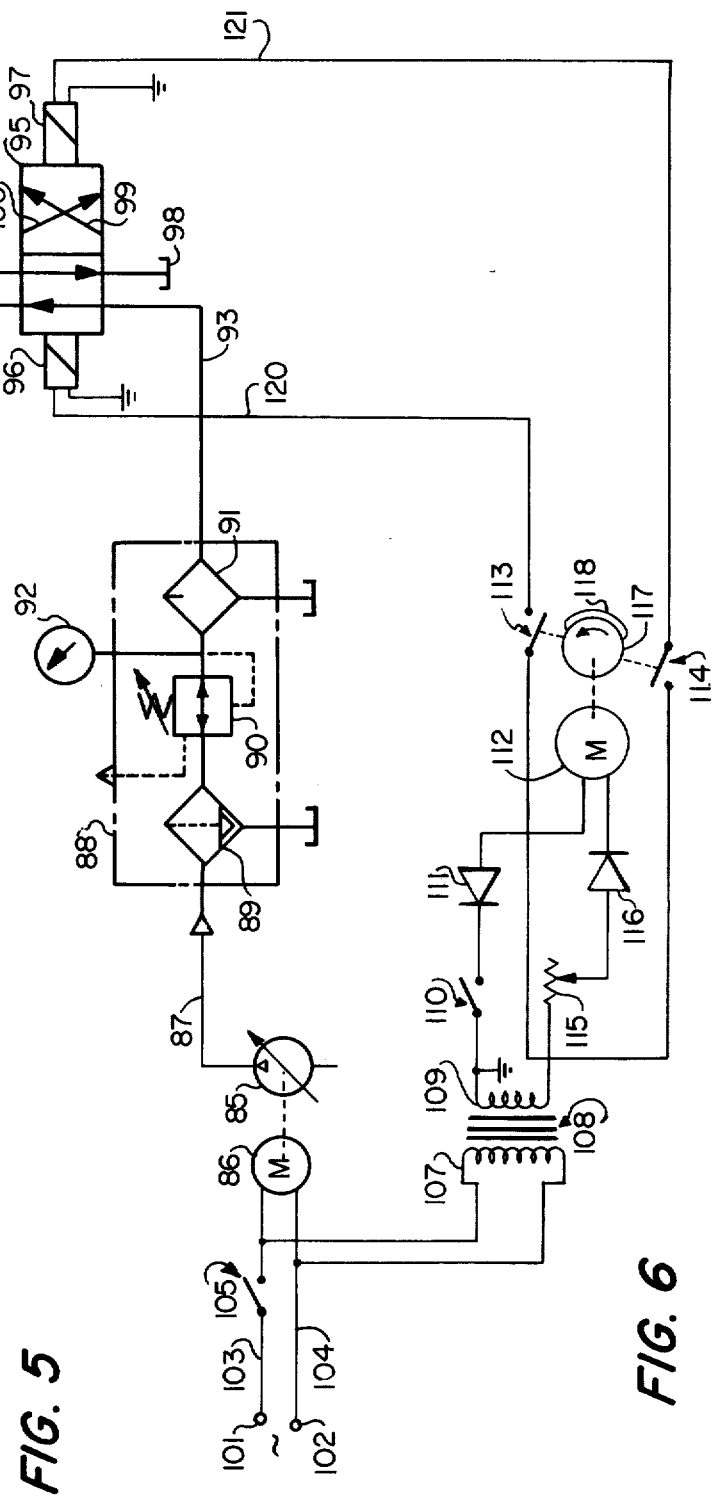
FIG. 6 is a schematic pneumatic diagram of drive means usable with the apparatus of FIGS. 1–5 to apply external force to a piston and cylinder arrangement to flex a joint.

A powered embodiment of the invention is illustrated in FIG. 6 which is schematic in nature, showing the fluid and electrical circuits but not illustrating the specific structure. The piston and cylinder arrangement and the attachment to the body are substantially identical to that of FIGS. 1–4 and need not be repeated.

In FIG. 6 there is shown a cylinder 75 having contained therein a piston 76 with a connecting rod 77, the end of rod 77 being connected to a pivot point 78 which will be regarded as equivalent to pivot point 21 of FIGS. 1 and 2. The end of the cylinder is connected to a pivot point 79 which will be regarded as equivalent to pivot point 20 in FIGS. 1 and 2. The cylinder is provided with check valves 80 and 81 which function as described with reference to FIG. 5. Fluid conduits 82 and 83 are connected to opposite ends of the cylinder through connectors of the type described with reference to FIG. 4.

The fluid supply and control apparatus for selectively applying fluid under pressure to conduits 82 and 83 includes a variable air pressure output compressor 85 which is driven by mechanical connection to an electrical motor 86. The compressed air output of the compressor is provided on a conduit 87 to suitable filtering, regulating and lubricating apparatus indicated schematically at 88. This unit includes a filter and separator 89, and adjustable pressure regulator 90 and a lubricator 91 and can also include a pressure gauge 92. These devices, in themselves, are conventional in nature and will not be further described. However, it will be noted that the regulation of pressure is important to prevent any possibility of physical harm to the patient and that the separation and lubrication of the compressed air is important to assure reliability and proper functioning of the system.

The filtered, regulated and lubricated compressed air is supplied on a conduit 93 to a solenoid operated, finite position, two position valve 95. Valve 95 is operated by solenoids 96 and 97, solenoid 96 being energizable to move the valve to the position illustrated and solenoid 97 being operative when energized to move the valve to the opposite position. In the position shown, pressure supplied on conduit 93 is conducted through the valve to conduit 82 and conduit 83 is vented to a reservoir 98 or atmosphere. When solenoid 97 is energized, compressed air supplied on conduit 93 is conducted through a path 99 to conduit 83 while conduit 82 is vented through a path 100 to reservoir 98 or atmosphere.

Solenoids 96 and 97 are operated by energization of their windings from an electrical circuit which will now be described. A source of electrical energy such as line voltage is connected to terminals 101 and 102 to which electrical conductors 103 and 104 are attached. Conductor 103 is connected through an on-off switch indicated generally at 105 to motor 86 and to one terminal of a primary winding 107 of a voltage reducing transformer indicated generally at 108. Terminal 104 is connected to the other terminal hub motor 86 and to the other terminal winding 107. Transformer 108 is a stepdown transformer to reduce the voltage from line voltage to a convenient level such as 24 volts on secondary winding 109. One terminal of winding 109 is connected through an on-off switch indicated generally at 110, which can be mechanically coupled to switch 105, the other side of the switch being connected to the anode of a conventional rectifying diode 111. The cathode of diode 111 is connected to one terminal of a d.c. timing motor 112. The other terminal of winding 109 is connected to one terminal of a normally open, momentary contact spring return microswitch indicated generally at 113, to one terminal of a similar momentary contact, spring return normally open microswitch 114 and to a variable speed control resistance 115. The movable wiper of resistance 115 is connected to the anode of a diode 116, the cathode of which is connected to the other terminal of motor 112. Diodes 111 and 116 provide rectification to operate d.c. motor 112.

A cam disc 117 is mechanically coupled to the driven shaft of motor 112 and rotated thereby in the direction of the arrow. Disc 117 carries a cam 118 which is adjustable with respect to the disc and timing motor and which is disposed to mechanically operate, in alternate fashion, switches 113 and 114. Those switches are connected to conductors 120 and 121, respectively, which are connected to solenoids 96 and 97, respectively, the other teminals of which are grounded.

The operation of the apparatus of FIG. 6 commences with the application of electrical energy to terminals 101 and 102 and the closing of switches 105 and 110. Motor 86 is thereby energized, activating compressor 85 to provide compressed air to valve 95 and motor 112 is energized to rotate the motor and its associated cam disc. Upon rotation of the motor, cam 118 contacts one of switches 113 and 114, closing the switch and providing electrical energy to one of the solenoids, causing motion of the valve to one of its two possible positions. Assuming that switch 113 is closed first, solenoid 96 is energized, moving the valve to the position shown, whereupon compressed air is applied through conduits 93 and 85 to the left end of cylinder 75 as shown in FIG. 6. Piston 76 is thereby forced to the right by the increased pressure in the left hand portion of cylinder 75, causing points 78 and 79 to be moved together and flexing the joint. When the timing motor rotates such that cam 118 encounters switch 114, voltage is provided on conductor 121 to energize solenoid 97, causing the valve 95 to move to the opposite position, applying pressure on conduit 83 and venting conduit 82. Piston 76 is thus moved to the left, moving points 78 and 79 apart and extending the joint.

It will be observed that there are several kinds of adjustment available to the physical therapist in employing this apparatus with a patient. First, the pressure to be applied to valve 95 and the piston and cylinder assembly is variable by adjusting the output of compressor 85 or the regulated output of regulator 90. Adjustment of this pressure controls the velocity of movement of the piston from one extreme position to the other. In addition, adjustment of variable resistance 115 controls the rotation speed of motor 112 and its associated cam disc and thereby alters the interval of time between the closing of switch 113 and the closing of switch 114. Thus, a dwell or rest interval at the end of each extension or flexion stroke can be obtained. As will be seen, when the piston arrives at the end of the cylinder, or the adjusted mechanical stop therein, no further motion is produced until the opposite switch is closed and valve 95 moved to its opposite position. This is a desirable and significant feature because it is often desirable in physical therapy to move the limb to one or the other of its extreme positions and permit it to rest there momentarily before initiating the opposite motion.

Other adjustment features can be incorporated but are not specifically disclosed herein. For example, the length of the connecting rod or attachments to the straps encircling the body can be provided with threaded coupling to alter the initial length of the apparatus as it is installed on the body. Additionally, a three-position valve and a more complex cam arrangement can be employed to provide an additional dwell at an intermediate point between the extreme flexion and extreme extension positions. Adjustment of the straps, as previously noted, can be employed to alter the angular extremes of flexion and extension as well as other variables dictated by variations between bodies of various patients.

While certain advantageous embodiments have been chosen to illustrate the invention, it will be understood by those skilled in the art that various changes and modifications can be made therein without departing from the scope of the invention as defined in the appendant claims.

What is claimed is:

1. A device for flexing and extending a body joint such as a knee or elbow comprising:
   first strap means for completely encircling the body near and on one side of the joint to be exercised;
   second strap means for completely encircling the body near and on the other side of the joint to be exercised;
   linkage means extending between said first strap means and said second strap means in predetermined relationship with the joint,
      said linkage means having a first link portion rigidly secured to said first strap means and a second link portion secured to said second strap means and means defining a pivot point connecting said link portions substantially aligned with the pivot axis of a joint to be exercised for permitting relative pivotal motion of said link portions, which motion corresponds with motion of a body portions joined at the joint to be exercised;
   fluid drive means connected between said first and second strap means to form the third side of a triangle with said first and second link portions for moving said strap means alternately toward and away from each other to flex and extend a body joint and, with said link portions, for minimizing compressive and extensive forces at the body joint;
   a source of fluid under pressure;
   valve and control means for controlling the application of fluid from said source to said drive means; and
   conduit means for interconnecting said source, said valve means and said drive means.

2. A device according to claim 1 wherein said fluid drive means includes:
   at least one pneumatic piston and cylinder assembly, the piston thereof being pivotally connected to said first strap means and the cylinder thereof being pivotally connected to said second strap means; and
   said source comprises an air compressor.

3. A device according to claim 2 wherein said valve and control means includes:
   a two position, four-way valve for alternately directing air under pressure to one and the other end of said cylinder;
   solenoid means for moving said valve;
   a source of electrical energy;
   timing switch means for selectively energizing said solenoid means; and
   circuit means for interconnecting said solenoid means, said source of energy and said timing switch means.

4. A device according to claim 3 wherein said valve and control means further includes:
   means for adjusting the pressure of air directed to said cylinder;
   wherein said solenoid means includes
   first and second solenoids, said first solenoid being operative, when energized, to move said valve to one of its two positions and said second solenoid being operative, when energized, to move said valve to the other of its two positions;
   and wherein said timing switch means includes
   first and second switches connected respectively to said first and second solenoids and to said source of energy to permit energization of said solenoids;
   a timing motor;
   adjustable speed control means for controlling the speed of said timing motor to permit alteration of the interval between successive energizations of said solenoids.

5. A device according to claim 2 wherein said piston and cylinder assembly includes:
   adjustable mechanical stop means for selectably limiting the extent of motion of the piston in the cylinder and thereby limiting the degree of flexion and extension of a joint being exercised.

* * * * *